(12) United States Patent
Batchinsky et al.

(10) Patent No.: US 12,171,927 B2
(45) Date of Patent: Dec. 24, 2024

(54) WEARABLE MODULAR EXTRACORPOREAL LIFE SUPPORT DEVICE FOR MOBILE TREATMENT OF SINGLE AND MULTIORGAN FAILURE

(71) Applicant: The Geneva Foundation, Tacoma, WA (US)

(72) Inventors: Andriy I. Batchinsky, San Antonio, TX (US); George T. Harea, San Antonio, TX (US); Daniel S. Wendorff, San Antonio, TX (US); Brendan M. Beely, San Antonio, TX (US); Teryn R. Roberts, San Antonio, TX (US)

(73) Assignee: The Geneva Foundation, Tacoma, WA (US)

( * ) Notice: Subject to any disclaimer, the term of this patent is extended or adjusted under 35 U.S.C. 154(b) by 0 days.

(21) Appl. No.: 18/200,119

(22) Filed: May 22, 2023

(65) Prior Publication Data
US 2023/0364316 A1  Nov. 16, 2023

Related U.S. Application Data

(62) Division of application No. 16/454,486, filed on Jun. 27, 2019, now Pat. No. 11,654,225.

(60) Provisional application No. 62/690,403, filed on Jun. 27, 2018.

(51) Int. Cl.
| | | |
|---|---|---|
| A61M 1/36 | (2006.01) | |
| A61B 5/00 | (2006.01) | |
| A61M 1/16 | (2006.01) | |
| A61M 1/34 | (2006.01) | |
| A61M 5/14 | (2006.01) | |
| A61M 5/142 | (2006.01) | |
| A61M 60/00 | (2021.01) | |
| A61M 60/113 | (2021.01) | |
| A61M 60/216 | (2021.01) | |
| A61M 60/232 | (2021.01) | |
| A61M 60/279 | (2021.01) | |
| A61M 60/31 | (2021.01) | |
| A61M 60/37 | (2021.01) | |
| A61M 60/38 | (2021.01) | |
| A61M 60/546 | (2021.01) | |

(52) U.S. Cl.
CPC ......... *A61M 1/3667* (2014.02); *A61B 5/6866* (2013.01); *A61B 5/6867* (2013.01); *A61M 1/16* (2013.01); *A61M 1/1698* (2013.01); *A61M 1/34* (2013.01); *A61M 1/3623* (2022.05); *A61M 1/3659* (2014.02); *A61M 1/3666* (2013.01); *A61M 5/14244* (2013.01); *A61M 60/00* (2021.01); *A61M 60/113* (2021.01); *A61M 60/216* (2021.01); *A61M 60/232* (2021.01); *A61M 60/279* (2021.01); *A61M 60/31* (2021.01); *A61M 60/37* (2021.01); *A61M 60/38* (2021.01); *A61M 60/546* (2021.01); *A61M 2205/8206* (2013.01); *A61M 2209/088* (2013.01)

(58) Field of Classification Search
CPC ........ A61M 1/16; A61M 1/1698; A61M 1/26; A61M 1/34; A61M 1/3659; A61M 1/3666; A61M 1/3667; A61M 5/14244; A61M 5/1723; A61M 60/00; A61M 2205/8206; A61M 2209/088; A61M 1/3623; A61M 1/2659; A61M 60/80; A61M 60/113; A61M 60/216; A61M 60/232; A61M 60/279; A61M 60/31; A61M 60/37; A61M 60/38; A61M 60/546; A61B 5/6866; A61B 5/6867
See application file for complete search history.

(56) References Cited

U.S. PATENT DOCUMENTS

| | | |
|---|---|---|
| 5,043,260 A | 8/1991 | Jauregui |
| 6,736,790 B2 | 5/2004 | Barbut et al. |
| 6,796,955 B2 | 9/2004 | O'Mahony et al. |
| 2004/0254514 A1 | 12/2004 | Gura |
| 2006/0241543 A1 | 10/2006 | Gura |
| 2008/0051689 A1 | 2/2008 | Gura et al. |
| 2010/0316694 A1 | 12/2010 | Mousa et al. |
| 2015/0034082 A1 | 2/2015 | Kimm et al. |
| 2015/0231323 A1 | 8/2015 | Spearman et al. |

(Continued)

FOREIGN PATENT DOCUMENTS

| | | |
|---|---|---|
| AU | 7475481 A | 3/1982 |
| CN | 103251993 A | 8/2013 |

(Continued)

OTHER PUBLICATIONS

Notice of Reasons for Rejection in Japanese Application No. 2020-573386, dated Sep. 20, 2023, 5 pages.

(Continued)

*Primary Examiner* — John Kim
(74) *Attorney, Agent, or Firm* — Finnegan, Henderson, Farabow, Garrett & Dunner, LLP

(57) ABSTRACT

In one exemplary embodiment, a wearable extracorporeal life support device includes a catheter fluidly connected to a pump and first and second modular extracorporeal life support components. The device may also be configured to be attached to a garment. The pump and the first and second modular extracorporeal life support components may be fluidly connected in series. The pump and the first and second modular extracorporeal life support components may also be fluidly connected in parallel. The first modular extracorporeal life support component may be a lung membrane and the second modular extracorporeal life support component may be a dialysis membrane.

9 Claims, 7 Drawing Sheets

(56) References Cited

U.S. PATENT DOCUMENTS

| | | |
|---|---|---|
| 2017/0252497 A1 | 9/2017 | Nosrati |
| 2017/0361007 A1 | 12/2017 | Roy et al. |
| 2018/0078688 A1 | 3/2018 | Svitek et al. |

FOREIGN PATENT DOCUMENTS

| | | |
|---|---|---|
| CN | 103946364 A | 7/2014 |
| DE | 40 28 311 C1 | 12/1991 |
| RU | 69 752 U1 | 1/2008 |
| WO | WO 01/70302 A1 | 9/2001 |
| WO | WO 2018/047956 A1 | 3/2018 |

OTHER PUBLICATIONS

Examination Report for European Application No. 19 826 438.4-1113, dated Oct. 17, 2023, 5 pages.

Office Action in Chinese Application No. 201980048772.3, dated Nov. 16, 2023, 22 pages.

Office Action in Korean Application No. 10-2021-7002048, dated Nov. 8, 2023, 5 pages.

Communication Pursuant to Article 94(3) EPC, European Application No. 19 826 438.4-1113, dated Feb. 8, 2023, 6 pages.

Decision to Grant, Russian Application No. 2021101561/14, dated Dec. 1, 2022, 18 pages.

Extended European Search Report for European Application No. 19826438.4-1113, dated Feb. 25, 2022, 7 pages.

First Examination Report, Indian Application No. 202127003596, dated Oct. 6, 2022, 7 pages.

First Official Action for Russian Application No. 2021101561/14, dated Oct. 6, 2021, 15 pages.

International Search Report for PCT/US2019/039441, dated Sep. 10, 2019, 2 pages.

Notice of Reasons for Rejection for Japanese Application No. 2020-573386, dated Mar. 29, 2023, 17 pages.

Office Action in Korean Application No. 10-2021-7002048, dated Jul. 5, 2023, 10 pages.

Search Report for Russian Application No. 2021101561/14, dated Oct. 4, 2021, 4 pages.

Second Official Action for Russian Application No. 2021101561/14, dated Apr. 4, 2022, 9 pages.

Written Opinion of the International Searching Authority for PCT/US2019/039441, dated Sep. 10, 2019, 7 pages.

Office Action in Israeli Application No. 305498, dated Dec. 12, 2023, 5 pages.

WEARABLE MODULAR EXTRACORPOREAL LIFE SUPPORT DEVICE FOR MOBILE TREATMENT OF SINGLE AND MULTIORGAN FAILURE

PRIORITY CLAIM

This application is a divisional application of U.S. application Ser. No. 16/454,486, filed Jun. 27, 2019, now U.S. Pat. No. 11,654,225, which claims priority from U.S. Provisional Application No. 62/690,403 filed Jun. 27, 2018, the contents of each of which are hereby incorporated by reference in their entirety.

TECHNICAL FIELD

The disclosed embodiments relate to the field of medical devices and, in particular, may include wearable devices for various forms of extracorporeal life support and methods of employing such devices. In some embodiments the wearable device combines extracorporeal membrane oxygenation and extracorporeal continuous renal replacement therapy but will equally apply to mobile support for liver, heart failure as well as selective brain perfusion and combinations thereof as part of multiorgan failure treatment/support. The device may also support use at home and outside medical facilities with self-operating end user characteristics.

BACKGROUND

Extracorporeal life support (ECLS) includes multiple forms of extracorporeal rescue therapies. It has typically denoted the use of prolonged extracorporeal cardiopulmonary bypass in patients with acute, reversible cardiac or respiratory failure. As technology has advanced, organ support functions other than gas exchange, such as liver, renal, cardiac support, have been provided by ECLS. In addition, ECLS has been used for organ harvesting in brain-dead donors and for prolonging viability of organs for transplantation, as well as being used to provide lung function for patients awaiting such transplantation.

Extracorporeal membrane oxygenation (ECMO) is one form of ECLS. ECMO is a technique of providing gas exchange outside of the body for those patients unable to provide an adequate amount of gas exchange or perfusion on their own. ECMO removes blood from the patient, removes carbon dioxide and oxygenates blood.

Extracorporeal membrane oxygenation has been used for severe respiratory failure in adult trauma patients for decades. Typically done through venovenous ECMO (VV ECMO) in which deoxygenated blood is drained from a large central vein and pumped through a gas exchange membrane before being returned to the central venous circulation (Cannon et al., 2018). In this configuration, the pulmonary circulation is not bypassed, and the heart does not get exposed to any significant change in preload or afterload.

In the hospital setting, patients with respiratory failure generally begin receiving mechanical ventilation (MV). Mechanical ventilators, are large machines which require the patient to be bedridden. The patient is also usually anesthetized or sedated, and may require medical paralysis, to receive mechanical ventilation. ECMO as used in hospitals is used as a last resort capability to attempt to salvage patients that no longer can be helped by mechanical ventilators or other treatments. The CESAR study (Efficacy and economic assessment of conventional ventilatory support versus extracorporeal membrane oxygenation for severe adult respiratory failure) has shown an improvement in 6-month survival without severe disability in patients getting ECMO versus conventional ventilation in patients with acute respiratory distress syndrome (Peek et al., 2009). The CESAR study was a multicenter, randomized controlled trial conducted in the United Kingdom that demonstrated a significant reduction in death and long-term disability in patients referred for management in an experienced ECMO center (Neff et al., 2013; Peek et al., 2009).

The confinement of the patient receiving mechanical ventilation and especially ECMO leads to a progressive deconditioning of muscles. The advancement of technology has led to the development of protocols for "ambulatory ECMO." These combine existing blood pumps and bypass oxygenators into an integrated system that can be wheeled behind the patient. Ambulatory ECMO has typically been used as a bridge to lung transplant, to hasten recovery by minimizing sedation and bed rest and allows patients to have physical therapy while awaiting an available lung. In most instances, conventional ECMO access is through the femoral vein, which makes ambulating dangerous as there is a risk of dislodging the catheter.

Extracorporeal life support (ECLS) also includes renal support. Acute kidney injury (AKI) is estimated to affect one in every five hospitalized patients worldwide and 40% of critically ill patients (Clemens et al, 2016). Even a small increase in serum creatinine (0.3-0.4 mg/dL) has been associated with an increased mortality, which then shows a stepwise progression with worsening renal function. Among survivors of AKI that require dialysis in the hospital, between 10% and 30% still require dialysis at hospital discharge (Heung et al., 2015). Chronic kidney disease or kidney failure can be fatal without dialysis or a kidney transplant.

The available modalities of renal replacement therapy include peritoneal dialysis (PD), intermittent hemodialysis (IHD), and continuous renal replacement therapies (CRRT). Peritoneal dialysis uses the peritoneum as a natural semipermeable membrane for diffusive removal of solutes. It is a very effective treatment modality in patients with chronic renal failure, and patient outcomes are at least equivalent to those treated with hemodialysis (Pannu et al., 2005). In adult patients, acute peritoneal dialysis is not widely used. The use of peritoneal dialysis is limited by both logistical and practical considerations (Pannu et al., 2005). Hemodialysis is a process of solute clearance based on diffusion across the membrane driven by a concentration gradient between the blood and dialysate. In general, intermittent dialysis is prescribed for three to six hours per treatment, with treatments multiple times per week (Pannu et al., 2005). Dialysis is typically performed in the hospital or in dialysis centers, where patients sit for a few hours, hooked up to large machines while their blood is filtered.

Continuous renal replacement therapy (CRRT) describes a variety of blood purification techniques that are intended to be applied twenty-four hours a day. The patient's blood is removed and pumped through a hemofilter, which resembles a dialyzer. CRRT helps prevent the hemodynamic fluctuations common with the more rapid IHD. Solute removal with CRRT is achieved either by convection (hemofiltration), diffusion (hemodialysis), or a combination of both these methods (hemodiafiltration). CRRT provides slower solute clearance per unit time as compared with intermittent therapies but over twenty-four hours may even exceed clearances with IHD (Pannu et al., 2005). The usual CRRT circuit involves a double lumen catheter, tubing to carry blood from patient's body through the catheter to the CRRT machine, CRRT machine and return tubing which sends the blood back to the patient's body. The most commonly applied modalities are continuous venovenous hemofiltration (CVVH), continuous venovenous hemodialysis (CVVHD), and continuous venovenous hemodiafiltration (CVVHDF). CRRT for the management of AKI and the resultant severe metabolic derangements has become commonplace in many trauma centers (Neff et al., 2009).

In the hospital setting, CRRT has also been used in combination with other extracorporeal therapies, including ECMO. It is common to see a decrease in urine output during ECMO that may be associated with acute kidney injury or acute renal failure. Patients with acute cardiopulmonary dysfunctions may be at high risk of developing acute kidney injury and fluid overload. In these patients, a renal replacement therapy is added, typically IHD or CRRT. Classic indications for initiation of renal replacement therapy in patients on ECMO include uremia, acidosis, electrolyte abnormalities, and fluid overload.

In some other hospitalized patients, they originally require dialysis and are placed on a renal replacement therapy, typically IHD or CRRT, and then develop secondary lung complications. In these patients, mechanical ventilation or ECMO is added.

In patients receiving both CRRT and ECMO, the most common technique is using separate vascular access for CRRT and for ECMO. This is typically done so that the CRRT and ECMO systems do not interfere with each other's hemodynamics.

The additional plastic lines of the circuitry increase the risk of blood clots because the primary cause of clotting on artificial surfaces is protein adsorption and platelet activation/aggregation. The additional lines also increase damage to blood as it is exposed to plastic due to contact activation of the inflammatory and coagulation cascades. This is especially true at low blood flow rates 250-500 ml/min of pumped blood through the ECLS system as at lower infusion rates blood is more likely to form clots on the surface of plastic. Although less pronounced, this problem persists in high flow (1-5 L min) conditions.

To minimize thrombotic complications and reduce platelet loss during exposure of blood to plastic the current approach is to infuse heparin which inactivates thrombin and subsequently reduces clot formation. However, this often leads to bleeding complications which, just as thrombotic complications are, not desirable, especially in trauma patients whom may bleed already.

The advanced technology of centrifugal pump-driven venoarterial and venovenous lung assistance made it possible to bring the ECMO technology to deployed soldiers in military hospitals (Neff et al., 2013). It has also allowed deployed soldiers to be transported to the United States while still on ECMO (Neff et al., 2013).

"Partial lung support" is a method of assisting lung ventilation and oxygenation to a lesser degree than complete mechanical ventilation and is accomplished by altering blood and gas flow through a polymer gas-exchange filter known as a lung membrane (Neff et al., 2013). At lower blood flow rates (<1,000 mL/min), significant $CO_2$ removal is possible, although physiologically significant oxygenation is unattainable. Changes in the flow of gas through the lung membrane can regulate the amount of $CO_2$ removal while maintaining constant blood flow through the circuit. Using this approach up to 50% of metabolically produced CO2 can be removed (Batchinsky et. al 2011).

Partial lung support early after injury can lead to improved outcomes for patients without access to mechanical ventilation. The blood flow rates for these systems is relatively low (e.g., 500-1,000 mL/min as compared to 5 L/min for full ECMO) and so a vascular access catheter can be placed easily using standard ultrasound-guided Seldinger technique (Cannon et al., 2018).

Continuous hemofiltration has also been demonstrated to improve outcomes in patients that sustain injury during combat operations and develop AKI (Neff et al., 2013).

The equipment used in the for partial lung support or continuous hemofiltration in the hospital setting, as well as for military use for deployed soldiers, is large and bulky. It does not allow for continuation of care outside of the hospital or outside of a specialized dialysis center. It is important to develop devices for continuation of care outside of the hospital that are mobile and wearable and require less oversight by medical personal. Every day about 10,000 people turn 65 years old which justifies the need to find out-of-hospital/home care treatment options for the aging population, which will require forms of lung, renal, or other organ support. Developments such as paracorporeal left ventricular assist devices (LVADs) for heart failure patients and continuous positive airway pressure (CPAP) ventilators for patients with sleep apnea have shown the success of these devices. A similar or larger impact in the aging population is envisioned using the device of the disclosed embodiments.

SUMMARY

The disclosed embodiments may include a device that permits wearable, mobile, at home, or outside hospitals, modular, organ support, organ replacement, and continuous extracorporeal life support. The device may, for example, provide respiratory support to the patient while conscious and without the need to be intubated and mechanically ventilated, anesthetized, incapacitated, and bedridden. The device may also allow, for example, ambulatory, extracorporeal $CO_2$ removal, partial oxygenation, and partial lung support through use of a lung membrane. The disclosed embodiments of the device may also allow, for example, ambulatory, or home use, extracorporeal removal of metabolites, cytokines, inflammatory mediators, pathogens and other blood contained compounds through use of a dialysis membrane. The device may also allow for concomitant use of the lung membrane and dialysis membrane, or other organ support device connected to the device in any order. The disclosed embodiments may provide organ support or organ replacement modules, devices, and/or components. Disclosed embodiments may provide organ replacement or organ support for lung(s), renal or kidney, liver, heart, brain (via dedicated selective perfusion of brain), gut (e.g. stomach or other abdominal organs), or combinations thereof. Additionally, the disclosed embodiments may provide integrated partial or total organ support, organ systems support, multisystem organ support and selective organ-specific or combination organ systems support for any amount of organs in any combination or grouping of support. Disclosed embodiments may provide for organ harvesting in brain-dead donors and for prolonging viability of organs for transplantation. For example, prolonging lung function, or other bodily functions for patients awaiting transplantation.

The disclosed embodiments may include a wearable device for extracorporeal life support of a patient comprising: a catheter fluidly connected to a pump and first and second, third, etc. modular extracorporeal life support components; wherein the pump and the first and second, third etc. modular extracorporeal life support components are configured to be attached to a garment or external reinforced body support construct (e.g. exoskeleton).

In at least some embodiments, the pump, first modular extracorporeal life support component, and second or third etc. modular extracorporeal life support components may be fluidly connected in series. In at least some embodiments, at least one of the pump, first modular extracorporeal life support component, and second modular extracorporeal life support component may be fluidly connected in parallel. Combinations of in series and parallel connections are envisioned in any particular order with a selector of support for organ(s) as required by patient condition or treatment goals.

In at least some embodiments, the first modular extracorporeal life support component may be a lung membrane. In at least some embodiments, the second modular extracorporeal life support component may be a dialysis membrane. Reverse order or other combinations for organs and organ systems is envisioned.

In at least some embodiments, the device may further comprise a battery, a power source, or generator of energy of any design.

In at least some embodiments, a portion of the catheter may be inserted into the jugular vein or other major vein or artery in the body. In at least some embodiments, the at least a portion of the catheter inserted into the jugular vein is advanced into the superior and inferior vena cava.

The disclosed embodiments may include a method of providing mobile ambulatory or at home, outside of hospital or treatment facility extracorporeal life support comprising pumping blood of a patient into first and second modular extracorporeal life support components via a pump; wherein the pump and first and second modular extracorporeal life support components are fluidly connected in series, in parallel or other combinations of connections in case of multiple organ support functionality; and wherein the pump and first and second modular extracorporeal life support components are configured to be attached to a garment to include exoskeleton or external supporting structures of any kind.

The disclosed embodiments may include a method of providing mobile ambulatory extracorporeal life support comprising: pumping deoxygenated blood of a patient through a first line to a pump; pumping deoxygenated blood to a lung membrane where the blood is oxygenated and carbon dioxide is removed; pumping oxygenated blood from the lung membrane to a dialysis membrane where the blood is filtered; returning blood to the patient through a second line or the same line. Disclosed embodiments provide mobile extracorporeal life support, such as during transport of patients between hospitals or from hospital to home or from home to hospital; as well as at home use or use outside of a treatment facility and or hospital in general. In a non-limiting example, embodiments of the present disclosure provide patient's with home dialysis, and not be dependent on hospitals or the need to travel or be admitted to a treatment facility.

The disclosed embodiments may include a method of providing anticoagulation in extracorporeal life support comprising: pumping blood of a patient through an extracorporeal circuit; pumping blood to a lung membrane and dialysis membrane in the extracorporeal circuit; infusing citrate or other anticoagulant agents into the blood in the extracorporeal circuit (e.g. unfractionated heparin "UFH", direct thrombin inhibitors "DTIs", anti-platelet agents, etc.); and returning blood to the patient, or using another form of anticoagulation and thrombosis mitigation via either coating the ECLS system with blood repellent or blood modifying agents; or embedding such agents within the polymers that construct the circuit.

As used herein the term "garment" refers to any item of clothing, such as, but not limited to, a vest exoskeleton or other external support constructs/structures of any design.

As used herein the term "catheter" refers to an intravenous catheter, a venous catheter, cannula, or any tube for peripheral access to the body, such as, but not limited to, a dual lumen catheter.

As applicable to other ways to removing blood from the body an arterial catheter may be used (catheter, cannula, or any tube for peripheral access to the body via any artery in the body, such as, but not limited to, a dual lumen catheter, or other catheter designs).

As applicable to other ways to removing blood from the body a combination of an arterial catheter with a venous catheter or peripheral vessel cannulation may be used (catheter, cannula, or any tube for peripheral access to the body via any artery in the body, such as, but not limited to, a dual lumen catheter, or other catheter designs inserted in cubital or femoral vein).

As used herein the term "lung membrane" refers to an oxygenator, membrane oxygenator, lung replacement membrane, artificial lung, or any device used to add oxygen to, and remove carbon dioxide from the blood, for example.

As used herein the term "dialysis membrane" refers to a dialysis filter, dialysis replacement membrane, renal replacement membrane, artificial kidney, dialyzer, or any device used to remove metabolites (e.g., lactate, myoglobin, creatinine etc.), inflammatory mediators, cytokines, or pathogens, for example.

As used herein the term "liver membrane" refers to a dialysis filter for liver dialysis, liver replacement membrane, artificial liver, dialyzer, or any device used to remove toxins (e.g., ammonia, phenylalanine, tyrosine, or albumin-bound substances such as bilirubin, bile acids, metabolites of aromatic amino acids, medium-chain fatty acids and cytokines), for example.

As used herein the term selective gut or brain perfusion system refers to either exclusively supporting the gut or brain by selective perfusion of them or combination of either or both with other organ system support.

The disclosed embodiments may include a wearable device for extracorporeal life support of a patient including modular components for providing life support. The modular components may be small enough to be carried or worn by the patient continuously and be used at home, outside of treatment facilities of during execution of daily tasks outside the home. In some embodiments, the device may be used to provide continuous treatment because the device may stay with the patient at all times In at least some embodiments, the device may include a catheter may provide venovenous access inserted via the right jugular vein. The catheter may be for the delivery and/or removal of fluid from the body. The catheter may have two holes to allow draining blood from the superior vena cava and from the inferior vena cava. One lumen may allow for deoxygenated blood to be removed from the body, while the other lumen may allow for oxygenated blood to return to the body. Other catheter designs including additional catheter lumens (2.3 4 etc.) or groups of holes are envisioned.

Cannulation in femoral vessels is possible although jugular is desirable to maintain mobility. The access through the jugular vein may allow for more efficient gas exchange then if access was through the femoral vein. This is partially because the jugular vein can accommodate larger catheters but also because jugular vein is a central vein and provides immediate access and blood delivery to the heart rather than a peripheral vein. Besides, in case of combat trauma and motor vehicle accidents, cannulation of jugular vein may be the preferred option due to missing limbs due to traumatic amputations.

The access through the jugular vein may also allow for a reduction in the length of the lines from the placement of the catheter in the jugular vein to a component of the device when compared to placement of the catheter in the femoral vein. The reduction in the length of the lines may allow for less blood to be activated and potentially damaged from being exposed to plastic. The reduction in the length of the lines may also allow for smaller pressures through the circuit, as well as smaller volumes of fluid necessary to prime the system before use. Reducing the length of lines also reduces the total volume of blood that is outside the body at any one time, which may help avoid derangements in blood pressure that are possible with extracorporeal blood systems.

In another embodiment of the device, the length of the connection between the catheter and a component of the device in the circuit may be adjustable, for example to the shortest possible length to include merging of multiple capabilities and modules into a single device carrying out different organ support functions.

In another embodiment, the device may include a pump. The pump may be but not limited to a roller pump, impeller pump, diagonal pump, or centrifugal pump or any blood propelling/sucking device. The pump may propel blood by means of suction from one of the ports of the dual lumen catheter and through one of the lines, for example. The pump may be fluidly connected to the component. In another embodiment, the pump may support a patient with reduced heart function or heart failure, for example.

In another embodiment, the device may include a lung membrane component. Blood flow to the lung membrane may be controlled by the pump. Gas exchange in the lung membrane may be determined by the permeability of the membrane to oxygen and carbon dioxide (their diffusion coefficients), the available membrane surface area, the pressure gradient for oxygen or carbon dioxide between the gas compartment and the blood, and the amount of time gas and blood interface across the membrane. Countercurrent gas and blood flows in the lung membrane may provide optimal gas exchange by maintaining the pressure gradient for oxygen transfer from gas to blood along the entire length of the membrane surface. Up to 50% of $CO_2$ produced the body may be removed by the lung membrane and adjusted as needed but higher efficiency is also envisioned with updated catheters/lines or larger size catheter/lines In another embodiment, the lung membrane may include an input for sweep gas. In some embodiments, the sweep gas may be ambient air either alone or enriched with other compounds/gasses. In some other embodiments, the sweep gas may be oxygen, from an oxygen tank or generated by a small compressor, for example.

In another embodiment, the design of the lung membrane may also include a heat exchanger to heat or cool the blood by convection.

In another embodiment, the device may also include a dialysis membrane. The dialysis membrane removes cytokines and inflammatory mediators and pathogens and metabolites from the blood. The dialysate is input through an inlet line and passes through the dialysis membrane; the effluent is output from the dialysis membrane through an outlet line.

In another embodiment, the device may include a liver membrane component. The liver membrane removes toxins from the blood. The liver membrane may support a patient with reduced liver function.

In another embodiment, blood may be returned to the patient through a second line to the second lumen of the jugular catheter and may infuse blood into the right atrium.

In another embodiment, the device may also allow for concomitant use of the lung membrane component and dialysis membrane component. In some embodiments, the pump, lung membrane, and dialysis membrane may be in series, in parallel, or in combinations thereof. For example, the pump may be in series with the lung membrane and dialysis membrane in parallel. By way of another example, the pump, lung membrane, and dialysis membrane may be in series with the dialysis membrane receiving oxygenated blood from the lung membrane. In yet other examples, the three components may be in series with the dialysis membrane receiving deoxygenated blood from the patient and providing filtered blood to the pump and lung membrane.

In another embodiment of the device, citrate anticoagulation of the dialysis membrane may be used to avoid the need to administer heparin for purposes of anticoagulation, as anticoagulation is carried out in the dialysis circuit and no systemic medication is given to the patient. In another embodiment, citrate anticoagulation of the lung membrane may be used to avoid the need to give heparin for purposes of anticoagulation. In another embodiment, citrate anticoagulation of both the lung membrane and dialysis membrane may be used to avoid the need to give heparin for purposes of anticoagulation. Thus, carrying out combination therapy with renal dialysis and lung support will lead to a new solution to the problem of anticoagulation in ECLS.

In another embodiment, fluids, medications, and diagnostic tests may be administered through the circuitry of the device either passively or via special retrieval or delivery devices/modules/tools.

In some embodiments, clamps may block flow through some or all of the tubing as an added safety measure.

In some embodiments, the device may include a power source, for example a battery. The battery may power the pump and the compressor. The battery may have a charge life for approximately 8 hours of use. The battery may be interchangeable with other batteries.

In another embodiment, the pump and any modular components may be attached to a garment. In some embodiments, the power source may be attached to the garment. The components of the device may attach to the garment by snap, friction fit, hook, or any similar suitable manner. The components of the device may attach to the garment on the front, back, left, right, or any position on the garment that allows for comfortable movement by the patient.

In another embodiment, the garment may be worn on an upper body of the patient. In another embodiment, the garment may be wearable under other garments. In another embodiment, the garment may be, for example, a vest.

In another embodiment, the device may be used to treat a patient with acute or chronic lung failure. The acute or chronic lung failure may include acute respiratory distress syndrome, chronic obstructive pulmonary disease (COPD), emphysema, bronchitis, or acute lung injury stemming from trauma and resuscitation, smoke inhalation and burns, pulmonary contusion, chemical weapons, blast injury, or other causes such as infection.

In another embodiment, the device may be used to control the levels of CO2 in circulating blood with the aim to optimize cerebral/brain perfusion pressure. In this case CO2 values would be obtained via in-line sensing technology embedded into the device and used to adjust blood flow and sweep gas flow in the device to achieve higher or lower CO2 levels in the blood.

In another embodiment, the device may be used to treat a patient with acute or chronic renal failure.

In another embodiment, the device may be used to treat a patient with acute or chronic liver failure.

In another embodiment, the device may be used to treat a patient with acute or chronic heart failure.

In another embodiment, the device may be used to perfuse the head and brain selectively to treat a patient with traumatic brain injury or optimization of blood supply to the brain with and without traumatic brain injury present, via accurate control of circulating CO2 levels in blood.

In another embodiment, the device may allow for early initiation of partial lung support. The device may allow for initiating partial lung support prior to a patient's need for a mechanical ventilator. The device may allow for hybrid breathing wherein the patient is partially able to breathe naturally while also receiving support from the device. The device may prevent the need to anesthetize and intubate the patient while providing treatment.

In another embodiment, by avoiding the need for intubation and mechanical ventilation, the device may also allow coughing, sneezing, or other natural clearance of the patient's airway.

In some embodiments, use of the device may remove the need for handovers between different services. In some embodiments, use of the device may eliminate the need to change equipment during medical transport between the point of initiation of the support, a hospital or within departments of the hospital or at home during autonomous use of the device by the patient outside a hospital or treatment center In some embodiments, the device may be used to provide early treatment to military personnel injured in the field. The device may be used to provide treatment at or near the point of injury in the field.

In some embodiments, the device may be used to provide early treatment to civilian personnel injured in the field during individual trauma or motor vehicle accidents or during mass casualty situations. The device may be used to provide treatment at or near the point of injury in the field or ambulatory support or at home use.

In another embodiment, the device may be used to treat chronic lung failure at home or outside a treatment center or hospital by $CO_2$ removal and partial oxygenation.

In some embodiments, the device may be used to carry out long term wearable multiorgan support with either selective organ perfusion or combination perfusion of several organs.

In another embodiment, the device may be used to treat lung failure by $CO_2$ removal and partial oxygenation.

In another embodiment, the device may treat renal failure while at a patient's home. The device may allow a patient to avoid going to a dialysis center or to a hospital. The device may allow for treatment without a medical personal's direct, continuous oversight.

In another embodiment, the device may include at least one sensor for measuring the oxygenation level of blood in the device. The device may include one or more sensors to measure the flow rate in the device. The device may include one or more sensors to measure pressures in the device. The device may include one or more sensors to identify air bubbles in the device.

In another embodiment, the pump may be controlled by a processor, for instance, a programmable logic controller, or other suitable controller, which can be easily programmed by the patient or a healthcare provider. Programming may be accomplished wirelessly, through a USB cable, using buttons, a touch screen, or other actuation and/or input mechanisms on the pump controller, or wirelessly, for example. For instance, a healthcare provider may be able to the device remotely through a wireless connection. This may provide an easy way for a physician or healthcare provider monitor the patient and make any necessary adjustments while outside of professional care settings.

In another embodiment, the pump and/or control system may provide information and/or feedback and/or readings to the patient or healthcare provider, through visual signals on a display or by automatic gathering and analysis of medical information with the purpose to assess, diagnose or predict which patient needs support to be initiated; which patient needs support to be stopped and which patient would benefit from which particular form of support.

By providing this consistent, on-demand mobile care, the device will remove the need for handovers between services and remove the need for changing equipment. Most importantly, providing a mobile, modular, wearable device for ambulatory extracorporeal support will prevent the need to anesthetize and intubate the patient while providing treatment.

BRIEF DESCRIPTION OF THE DRAWINGS

The accompanying drawings, which are incorporated in and constitute a part of this specification, illustrate disclosed embodiments and, together with the description, serve to explain the disclosed embodiments.

Annotations appearing in the figures are exemplary only, and are not restrictive of the invention as claimed.

DETAILED DESCRIPTION

Reference will now be made in detail to the present embodiments (exemplary embodiments) of the disclosure, examples of which are illustrated in the accompanying drawings.

Figure 1:
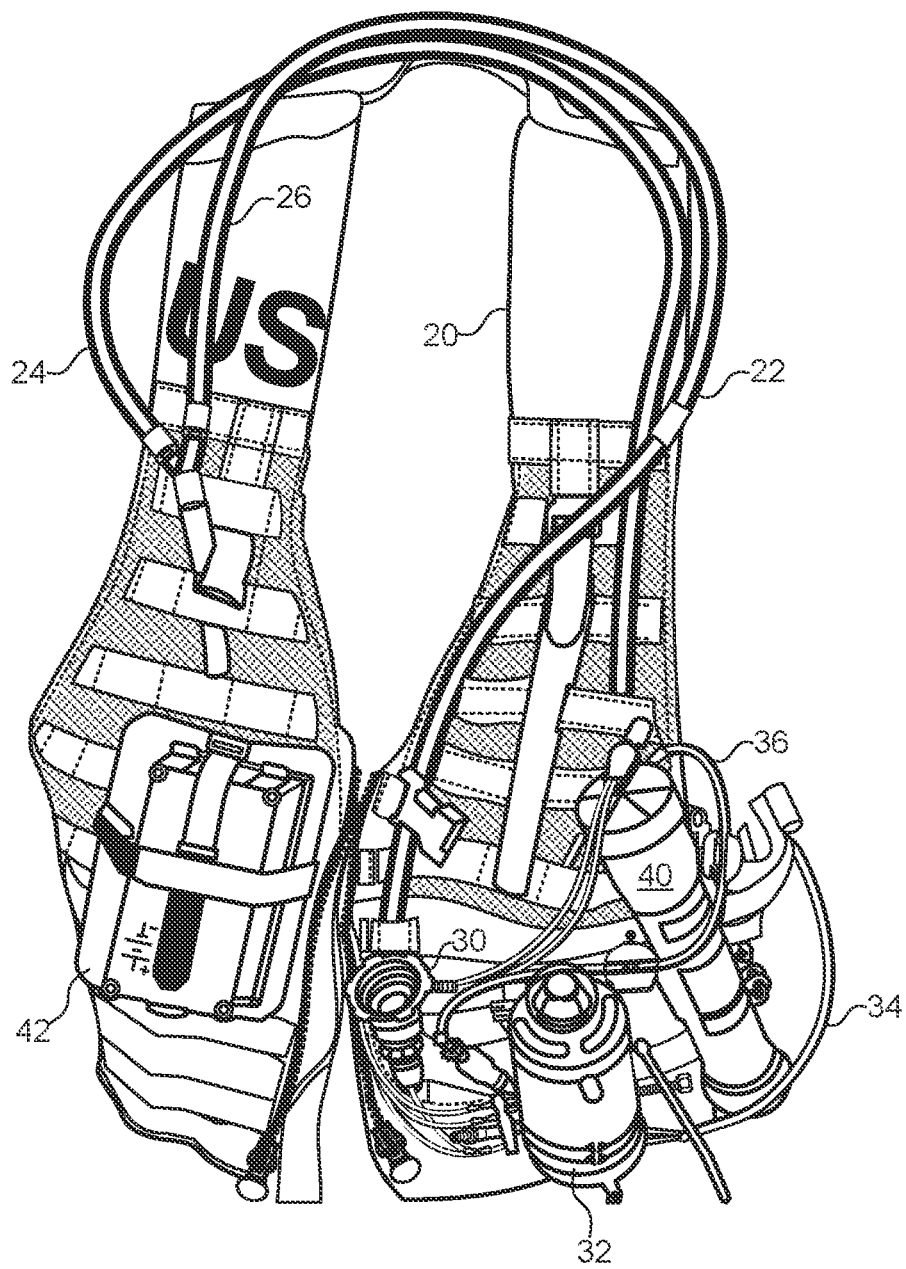
FIG. 1 is a photograph of an exemplary combination device, consistent with at least one of the disclosed embodiments.

FIG. 1 illustrates an exemplary wearable extracorporeal life support device 20 combining extracorporeal membrane oxygenation and extracorporeal continuous renal replacement therapy in accordance with at least some embodiments in accordance with the present disclosures. Identical or similar concepts will apply in case of adding other organ support membranes to the device. In some embodiments, the wearable extracorporeal life support device 20 may be a vest 20. A dual lumen catheter 22 may be inserted into a patient via the right jugular vein (not pictured), for example. The catheter 22 may have two holes to allow draining blood from the superior vena cava and from the inferior vena cava. One lumen (e.g. lumen 24) may allow for deoxygenated blood to be removed from the body, while the other lumen (e.g. lumen 26) may allow for oxygenated blood to return to the body.

In accordance with at least some embodiments of the present disclosure, the lines from the dual lumen catheter 22 may be attached to the vest 20, for example, in the front of the patient. In accordance at least some embodiments, the lines from the dual lumen catheter 22 may be attached to the vest 20 behind the patient's neck, or on the left or right side of the vest 20. In accordance at least some embodiments, the lines may be attached to the vest 20 at any other placement. In accordance with another embodiment, the lines may not be attached to the vest 20.

A pump 30 may propel blood by means of suction from one of the ports of the dual lumen catheter 22 and through one of the lines. The pump 30 may be fluidly connected to the inlet of a lung membrane 32. The inlet of the lung membrane 32 may also be fluidly connected to the catheter 22. The lung membrane 32 may remove $CO_2$ from the blood. The lung membrane 32 may also oxygenate the blood. The design of the lung membrane 32 may also include a heat exchanger to heat the blood by convection if a fluid warmer is available. In some embodiments, the lung membrane 32 may support a minimum of 500 ml/min flow using a ¼ inch tubing size and a 15 French (F) catheter and be also able to accommodate higher flow rates e.g. 1 Liter (L) per minute using an 18 F catheter; through 2 L per minute using a 23 F catheter for up to 4 liters per minute using a 32 F catheter and all using ½ inch tubing.

In another embodiment, the outlet of the lung membrane 32 may return blood through a second line to the second lumen of the dual-lumen catheter 22 (e.g. a jugular catheter) and may infuse blood into the right atrium.

In another embodiment, the lung membrane 32 may include an input for sweep gas to remove $CO_2$ and provide oxygenation. In some embodiments, a sweep gas line 34 may be connected to a small compressor mounted on the device 20 which will generate oxygen and cycle ambient air through the lung membrane 32 for the purposes of gas exchange. In some embodiments, the sweep gas line 34 may input ambient air to the lung membrane 32.

In another embodiment, a shunt line 36 may be connected to the inlet line, outlet line, in parallel, in series or other combination. The shunt line 36 may lead a side flow of blood from the lung membrane 32 into the inlet of a dialysis membrane 40. The dialysis membrane 40 may remove at least one of metabolites, inflammatory mediators, cytokines, and/or pathogens. This may be accomplished using various commonly established configurations of renal dialysis.

In another embodiment, the pump 30 may be fluidly connected to the dialysis membrane 40. The outlet of the dialysis membrane 40 may return blood through a second line to the second lumen of the dual-lumen catheter 22 and may infuse blood into the right atrium.

Although FIG. 1 shows a pump 30 connected to the lung membrane 32 and dialysis membrane 40 in series, various other configurations are contemplated, some of which are illustrated in FIGS. 2 through 7.

The lung membrane 32, dialysis membrane 40, and pump 30 may be attached to the vest 20 in the front, in the back, on the left, on the right, or in any possible placement on the vest 20.

In some embodiments. the device 20 may include a power source 42, for example a battery.

FIGS. 2 through 7 are illustrations of the various configurations of the pump 30, lung membrane 32, and dialysis membrane 40 in accordance with at least some embodiments of the present disclosure. In FIGS. 2 through 7 deoxygenated blood is represented by a dashed line and oxygenated blood is represented by a solid line.

Figure 2:
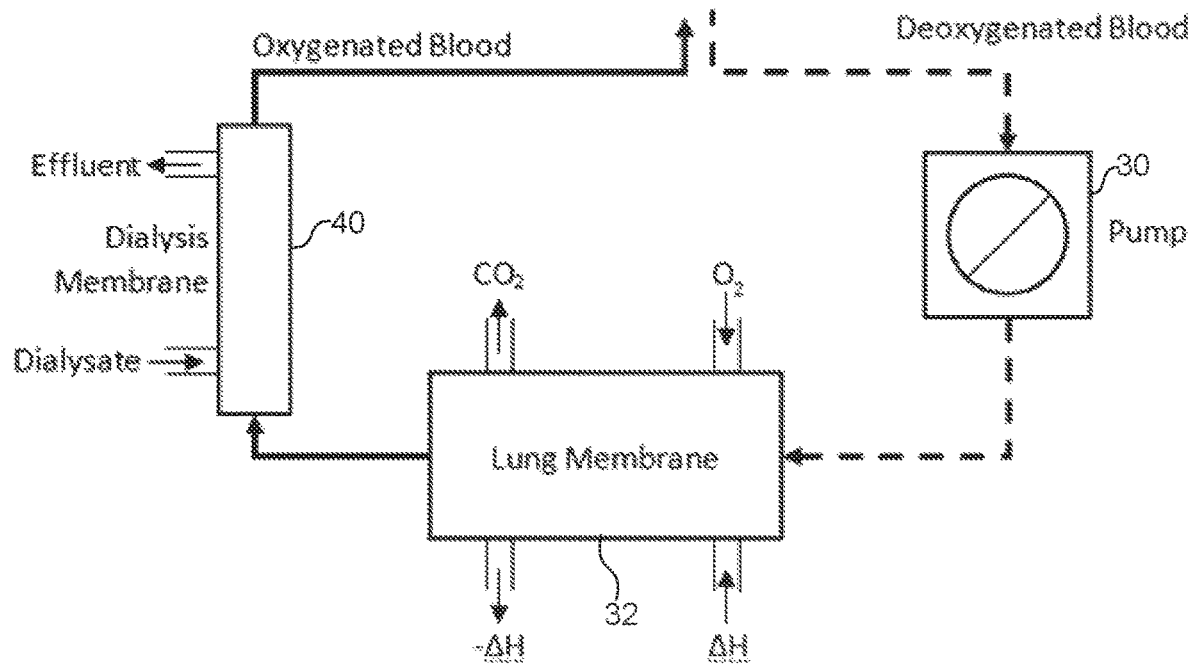
FIG. 2 is an illustration of the components, connections, and fluid flow path of an exemplary combination device in accordance with at least one of the disclosed embodiments.

FIG. 2 illustrates the pump 30, lung membrane 32, and dialysis membrane 40 in series. Deoxygenated blood enters the catheter 22 and enters the first line to the pump 30. Deoxygenated blood is then pumped to the lung membrane 32 where the blood is oxygenated, and carbon dioxide is removed. Oxygenated blood then enters the dialysis membrane 40 where at least one of metabolites, inflammatory mediators, cytokines, and/or pathogens are removed. Then the filtered and oxygenated blood is ultimately returned to the patient through the other line.

Figure 3:
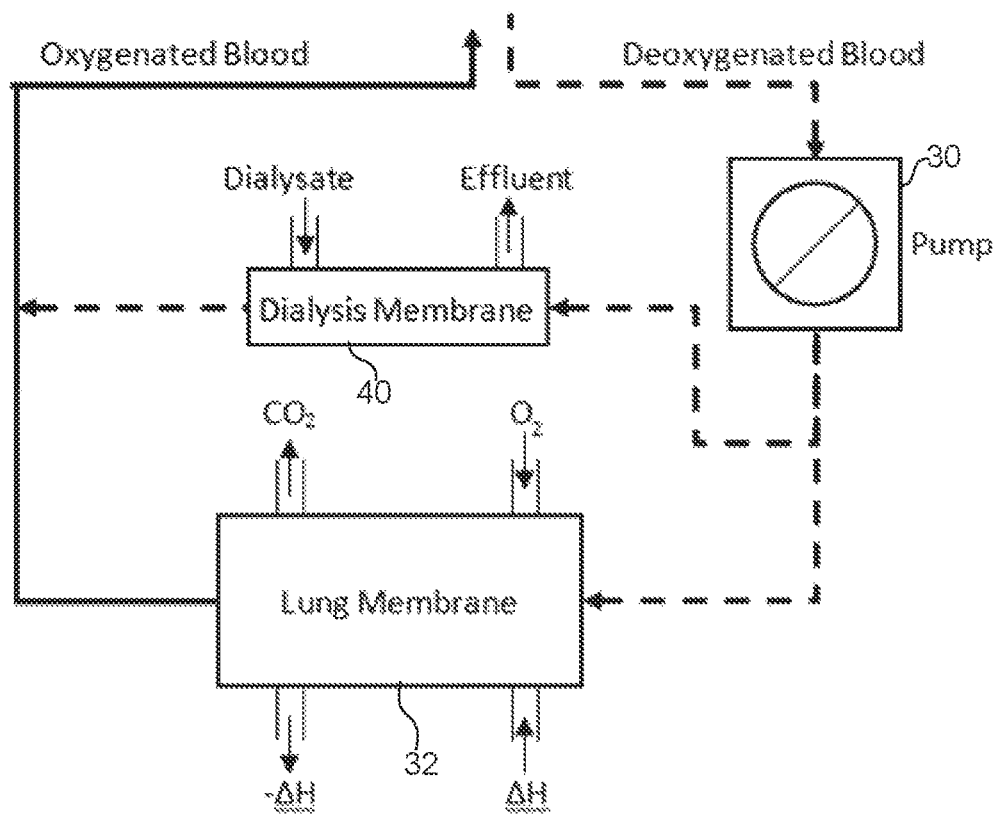
FIG. 3 is an illustration of components, connections, and fluid flow path of an exemplary combination device in accordance with at least one of the disclosed embodiments.

FIG. 3 illustrates the pump 30 in series with the lung membrane 32 and dialysis membrane 40 in parallel. Deoxygenated blood from the patient may enter the pump 30 and may be pumped in parallel to both the lung membrane 32 and dialysis membrane 40. Oxygenated blood from the lung membrane 32 may be joined with filtered, deoxygenated blood from the dialysis membrane 40 and returned to the patient in one line.

Figure 4:
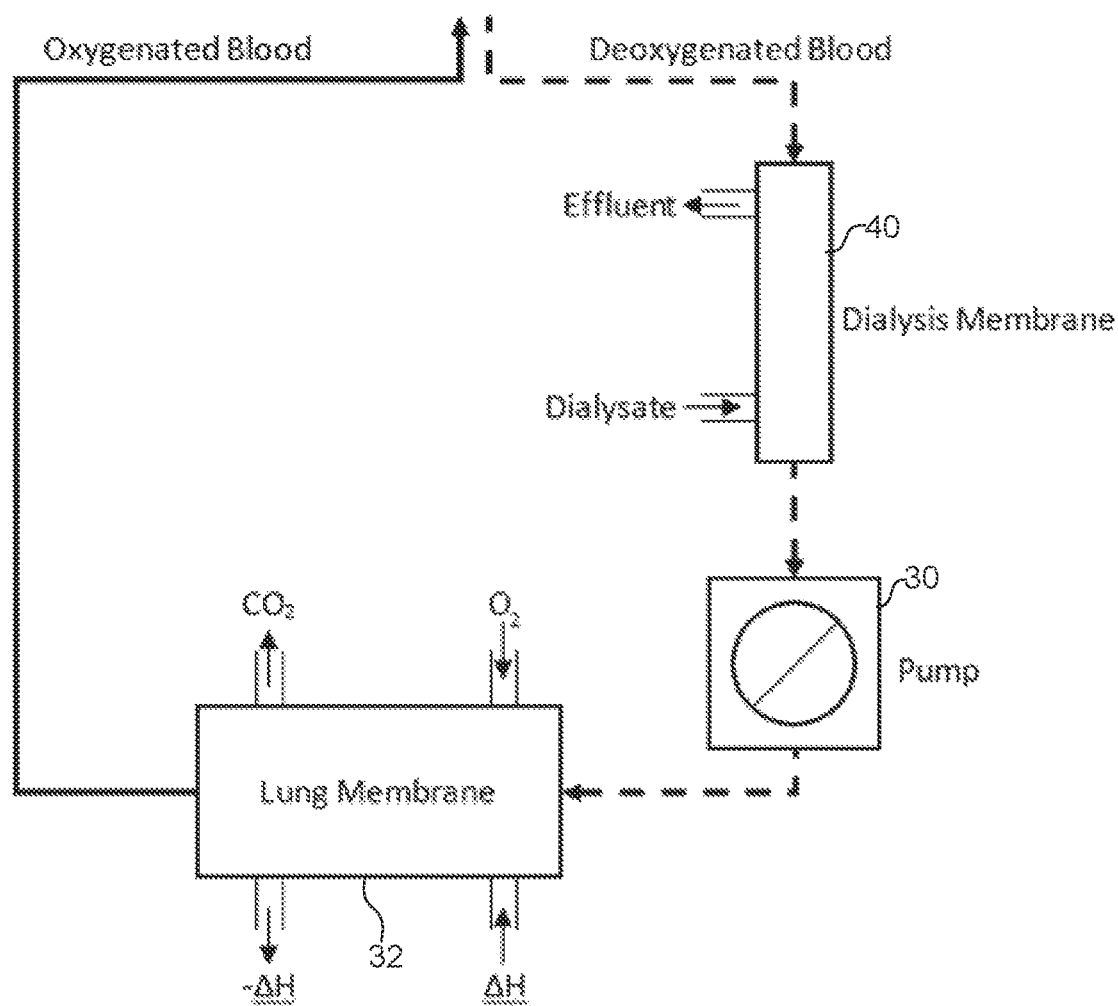
FIG. 4 is an illustration of the components, connections, and fluid flow path of an exemplary combination device in accordance with at least one of the disclosed embodiments.

FIG. 4 illustrates the dialysis membrane 40, pump 30, and lung membrane 32 in series. Deoxygenated blood from the patient may enter the dialysis membrane 40. Filtered, deoxygenated blood then enters the pump 30 and is pumped to the lung membrane 32. Oxygenated blood is then returned to the patient. In some embodiments, the series connection may provide direct control of flow through the dialysis membrane. Additionally, the series connection may simplify the tubing and connections of the system.

Figure 5:
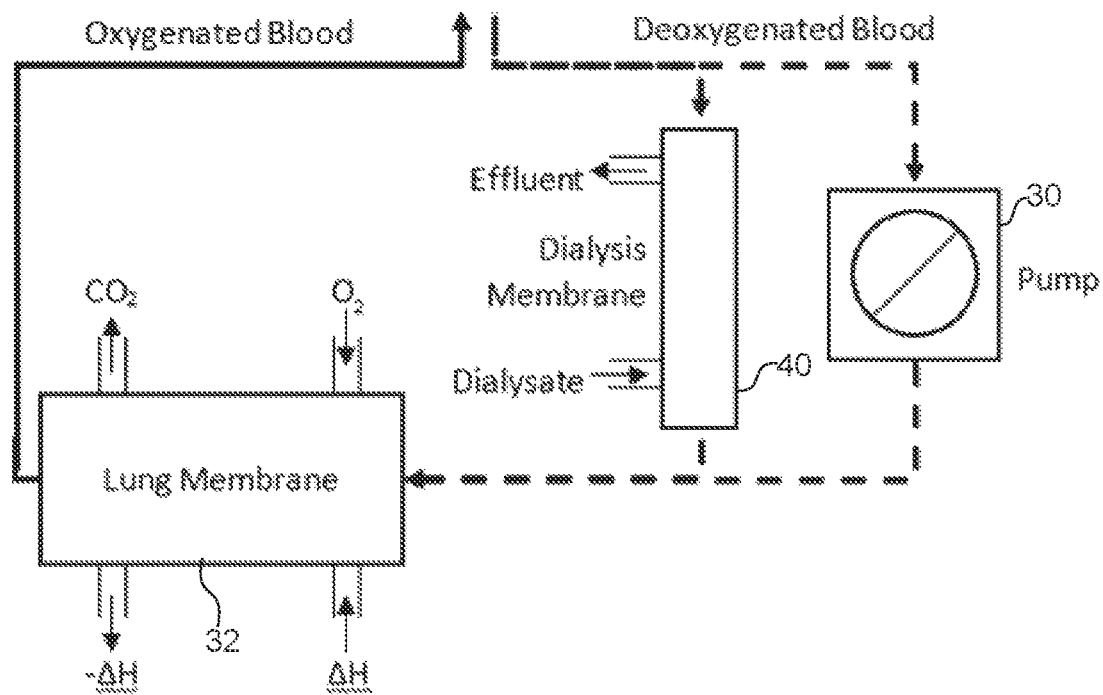
FIG. 5 is an illustration of the components, connections, and fluid flow path of an exemplary combination device in accordance with at least one of the disclosed embodiments.

FIG. 5 illustrates the pump 30 and dialysis membrane 40 in parallel with the lung membrane 32 in series. Deoxygenated blood from the patient may enter both the pump 30 and dialysis membrane 40 in parallel. Filtered blood from the dialysis membrane 40 may then be joined with blood from the pump 30 and pumped to the lung membrane 32. Oxygenated blood is then returned to the patient. In some embodiments, the parallel arrangement may be advantageous if one of the devices clots, the other device can operate independently or be exchanged for a different device. In some embodiments, blood may flow through one system at a time, e.g. through dialysis membrane 40 or through lung membrane 32. Accordingly, the parallel connection provides a modular design. Additionally, the parallel arrangement may provide lower fluid pressure in the dialysis membrane 40, which may be beneficial for maintenance of blood viability. For example, higher pressure may require turbulent flows and destruction of erythrocytes. In some embodiments, lung support may require higher blood flow than a maximum flow a dialysis membrane 40 may support. The parallel connection may permit independent blood flow regulation and flow through lung membrane 32 can be as high or low as needed, with independent regulation of flow through dialysis membrane 40. For example, the blood flow may range from 50 ml/min to 500 ml/min.

Figure 6:
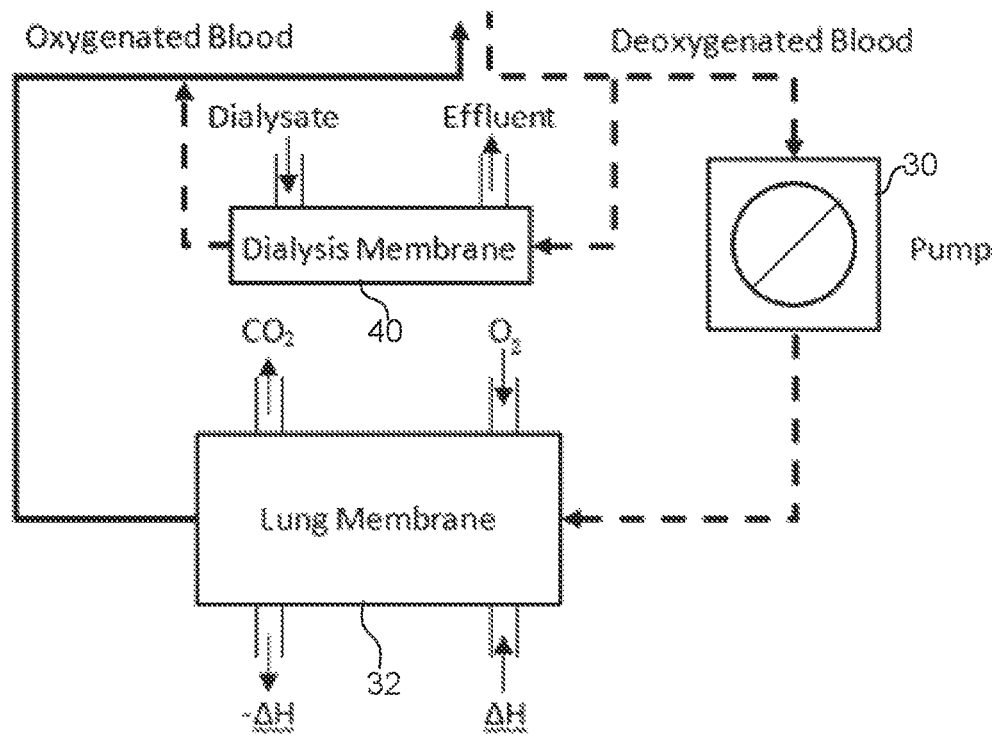
FIG. 6 is an illustration of the components, connections, and fluid flow path of an exemplary combination device in accordance with at least one of the disclosed embodiments.

FIG. 6 illustrates the dialysis membrane 40 in parallel with the pump 30 and lung membrane 32 in series. Deoxygenated blood from the patient may enter both the pump 30 and dialysis membrane 40 in parallel. The blood from the pump 30 is then pumped to the lung membrane 32. Oxygenated blood from the lung membrane 32 may be joined with filtered, deoxygenated blood from the dialysis membrane 40 and returned to the patient in one line.

Figure 7:
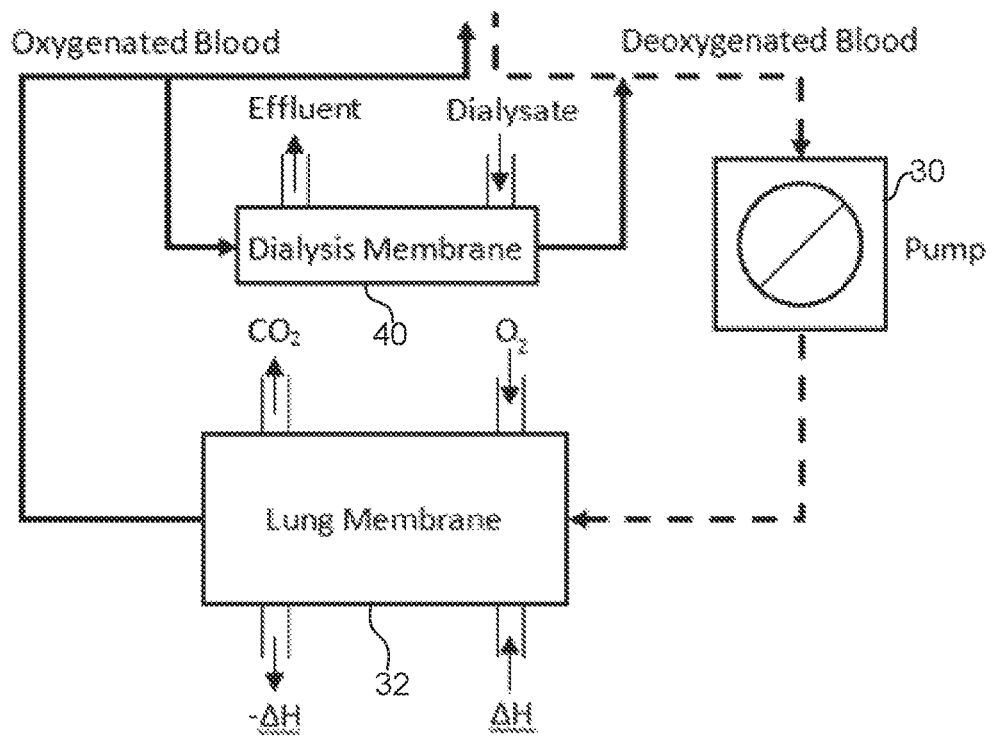
FIG. 7 is an illustration of the components, connections, and fluid flow path of an exemplary combination device in accordance with at least one of the disclosed embodiments.

FIG. 7 illustrates the dialysis membrane 40 in parallel with the pump 30 and lung membrane 32 in series. Deoxygenated blood from the patient may enter the pump 30 and may be pumped to the lung membrane 32. Oxygenated blood may then separately be returned to the patient and enter the dialysis membrane 40. Filtered blood from the dialysis membrane 40 may be joined with deoxygenated blood from the patient before entering the pump 30.

Although FIGS. 2 through 7 illustrate exemplary embodiments of the various configurations of the pump 30, lung membrane 32, and dialysis membrane 40, other configurations not illustrated are contemplated. In one embodiment, only the pump 30 and lung membrane 32 are used for patients requiring lung support and not renal support. In another embodiment only the pump 30 and dialysis membrane 40 are used for patients requiring renal support and not lung support.

Moreover, while illustrative embodiments have been described herein, the scope includes any and all embodiments having equivalent elements, modifications, omissions, combinations (e.g., of aspects across various embodiments), adaptations or alterations based on the present disclosure. The elements in the claims are to be interpreted broadly based on the language employed in the claims and not limited to examples described in the present specification or during the prosecution of the application, which examples are to be construed as non-exclusive. Further, the steps of the disclosed methods can be modified in any manner, including by reordering steps or inserting or deleting steps. It is intended, therefore, that the specification and examples be considered as example only, with a true scope and spirit being indicated by the following claims and their full scope of equivalents.

What is claimed is:

1. A method of providing mobile ambulatory extracorporeal life support comprising:
    pumping blood of a patient into first and second modular extracorporeal life support components via a pump;
    wherein the pump and first and second modular extracorporeal life support components are fluidly connected in series; and
    wherein the pump and first and second modular extracorporeal life support components are configured to be attached to a garment;
    further comprising a module to scavenge metabolites and/or hemoglobin;
    wherein the pump supports blood flow ranging from 500 ml/min to 4 L/min.

2. The method of claim 1, wherein the pump supports blood flow for pediatric patients.

3. The method of claim 1, wherein the pump supports blood flow for adult patients.

4. The method of claim 1, wherein the pump supports blood flow for tissues, organs, vascular composite allografts, and/or limbs of patients.

5. The method of claim 1, wherein the pump and first and second modular extracorporeal life support components are configured to concurrently provide support for a patient body and for tissues, organs, vascular composite allografts, and/or limbs of patients.

6. The method of claim 1, wherein the pump and first and second modular extracorporeal life support components are powered by a renewable energy source.

7. The method of claim 1, wherein the pump operates in a continuous flow or pulsatile flow mode.

8. The method of claim 1, wherein the first and second modular extracorporeal life support components, the pump, and the garment are connected by tubing to make up a circuitry, the length of the tubing being minimal.

9. A method of providing mobile ambulatory extracorporeal life support comprising:
    pumping blood of a patient into first and second modular extracorporeal life support components via a pump;
    wherein the pump and first and second modular extracorporeal life support components are fluidly connected in series; and
    wherein the pump and first and second modular extracorporeal life support components are configured to be carried and mounted on a device rather than worn;
    further comprising a module to scavenge metabolites and/or hemoglobin;
    wherein the pump supports blood flow ranging from 500 ml/min to 4 L/min.

* * * * *